(12) United States Patent
Vergari et al.

(10) Patent No.: US 10,932,913 B2
(45) Date of Patent: Mar. 2, 2021

(54) MULTI-LAYERED PROSTHETIC ELEMENT

(71) Applicant: MEDACTA INTERNATIONAL SA, Castel San Pietro (CH)

(72) Inventors: Enoc Vergari, Grandate (IT); Massimiliano Bernardoni, Figino (CH); Francesco Siccardi, Sonvico (CH); Alberto Siccardi, Sonvico (CH); David Manning, Chicago, IL (US); Dennis McGee, Boise, ID (US)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 0 days.

(21) Appl. No.: 15/128,659

(22) PCT Filed: Mar. 24, 2015

(86) PCT No.: PCT/IB2015/052142
§ 371 (c)(1),
(2) Date: Sep. 23, 2016

(87) PCT Pub. No.: WO2015/145348
PCT Pub. Date: Oct. 1, 2015

(65) Prior Publication Data
US 2018/0008416 A1    Jan. 11, 2018

(30) Foreign Application Priority Data
Mar. 27, 2014    (IT) .............................. MI2014A0516

(51) Int. Cl.
*A61F 2/28* (2006.01)
*A61F 2/30* (2006.01)
(Continued)

(52) U.S. Cl.
CPC .......... *A61F 2/30734* (2013.01); *A61F 2/389* (2013.01); *A61F 2002/30011* (2013.01);
(Continued)

(58) Field of Classification Search
CPC .... A61F 2/3859; A61F 2/389; A61F 2/30734; A61F 2002/30736; A61F 2/4684;
(Continued)

(56) References Cited

U.S. PATENT DOCUMENTS 8,382,849 B2 * 2/2013 Thomas .............. A61F 2/30734
623/16.11
8,506,645 B2    8/2013 Blaylock et al.
(Continued)

FOREIGN PATENT DOCUMENTS

EP    2130516 A1    12/2009
EP    2679201 A1    1/2014

*Primary Examiner* — Ann Schillinger
(74) *Attorney, Agent, or Firm* — Allen, Dyer, Doppelt + Gilchrist, P.A. Attorneys at Law

(57) ABSTRACT

A multi-layered prosthetic element comprises a central body (1; 1') of a substantially truncated conical shape and having a through axial cavity (2; 2') open at both ends which gives the central body (1; 1') a ring-shaped cross-section. The central body (1, 1') comprises an outer portion (110; 110'), made of trabecular metal material, an inner portion (130; 130'), made of trabecular metal material, and an intermediate portion (120; 120') made of metal material without significant porosity. The outer portion (110; 110') and the inner portion (130; 130') are integrally connected to the intermediate portion (120; 120'). The intermediate portion (120; 120') is configured to mechanically resist to stresses transmitted to the inner portion (130; 130') on one side and to the outer portion (110; 110') on the other side.

6 Claims, 6 Drawing Sheets

(51) Int. Cl.
*A61L 27/56* (2006.01)
*A61F 2/38* (2006.01)
*A61F 2/46* (2006.01)

(52) U.S. Cl.
CPC .............. *A61F 2002/3092* (2013.01); *A61F 2002/30125* (2013.01); *A61F 2002/30217* (2013.01); *A61F 2002/30324* (2013.01); *A61F 2002/30738* (2013.01); *A61F 2002/30971* (2013.01); *A61F 2002/4631* (2013.01)

(58) Field of Classification Search
CPC .............. A61F 2/461; A61F 2002/3863; A61F 2002/30604; A61F 2002/30616
See application file for complete search history.

(56) References Cited

U.S. PATENT DOCUMENTS

| | | |
|---|---|---|
| 2004/0162619 A1 | 8/2004 | Blaylock et al. |
| 2011/0009974 A1* | 1/2011 | Blaylock ............ A61B 17/1764 623/20.32 |
| 2012/0016482 A1 | 1/2012 | Mooradian et al. |
| 2013/0178947 A1* | 7/2013 | Monaghan ................ A61F 2/28 623/23.55 |

* cited by examiner

MULTI-LAYERED PROSTHETIC ELEMENT

RELATED APPLICATION

This application is based upon prior filed copending International Application No. PCT/IB2015/052142 filed Mar. 24, 2015, which claims priority to Italian Application No. MI2014A000516, filed Mar. 27, 2014, the entire subject matter of which is incorporated herein by reference in its entirety.

TECHNICAL FIELD

The present invention relates to a medical device, and more particularly, to a multi-layered prosthetic element.

BACKGROUND

Prosthetic joints are known in the art by which it is possible to fully or partly replace one or more joints of the human body. Usually, such joint prostheses comprise a receiving element, a first joint element, and a second joint element. The first and second joint elements are fixed at a distal part of a first bone, for example, a femur, and at a proximal part of a second bone, for example, a tibia, respectively. The receiver element is the interface between the two joint elements and receives the stresses imposed on it by the bone structure to the two joint elements.

Depending on the joint type involved in the replacing procedure, the three elements mentioned are different in terms of their shape and their type of interaction in order to fit perfectly to the specific movement of the joint and to the stresses imposed by the human body. Depending on the type of disease that affects the joint and/or on the extent of wear of the site in which the bone structure in the joint area is located, it may be necessary further elements in addition to the above mentioned elements in such a way as to ensure a perfect anchoring of the prosthesis to the bone structure, its correct positioning, and its proper functioning. One of the further elements has the function to strengthen the bone structure around the zone involved in the intervention. In fact, it is possible that the bones around the joint to be replaced are not able to receive, within them, part of the respective joint element. This phenomenon may be due to the fact that the bone formation involved in the insertion of the joint element has an insufficient thickness to withstand the loads transmitted by the prosthesis, or the bone formation appears to be shorter than its homolog as present in the healthy limb, making it necessary a re-balancing that will be achieved by the implantation of the prosthesis itself.

By way of explanatory example, consider a knee prosthesis by which one wishes to totally replace the natural joint of a patient by inserting an artificial prosthesis. In this case, it is possible that one of the femur and the tibia, or both, have structural deficiencies which make essential the insertion of an additional element in order to strengthen the bone structure which needs it. By analyzing in more detail, the possibility described above, assuming that the bone affected by structural deficiencies is the tibia, the procedure involves inserting inside it an additional element, the so-called filler, which is capable of give to the tibia the structural rigidity necessary for it to be able to withstand the loads transmitted to it by its respective joint element and to provide to the latter a solid anchoring base.

SUMMARY

Generally speaking, a multi-layered prosthetic element comprises a central body of a substantially truncated conical shape and having a through axial cavity open at both ends which gives the central body a ring-shaped cross-section. The central body comprises an outer portion, made of trabecular metal material, an inner portion, made of trabecular metal material, and an intermediate portion made of metal material without significant porosity. The outer portion and the inner portion are integrally connected to the intermediate portion. The intermediate portion is configured to mechanically resist to stresses transmitted to the inner portion on one side and to the outer portion on the other side.

DETAILED DESCRIPTION

Figure 1:
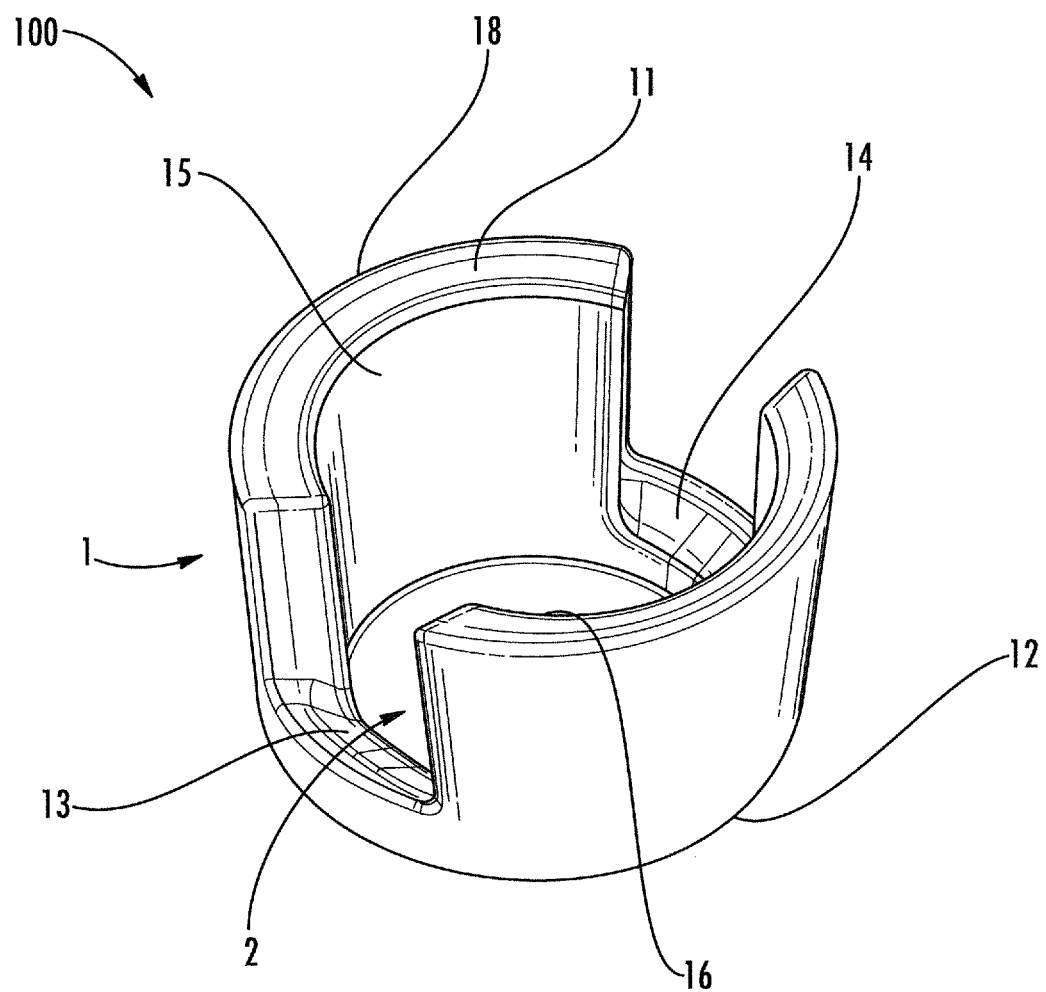
FIG. 1 is an isometric view of a first embodiment of the present invention.

Additional elements for use in cases of joint prosthetic implantation are known in the art. An example approach is disclosed in U.S. Pat. No. 8,506,645 to Blaylock et al., also assigned to Zimmer, Inc. The patent discloses a tibial filler for use in the implantation of a knee prosthesis. The tibial filler has a substantially annular shape with a proximal and a distal surface, an outer and an inner front surface, an inner and outer rear surface, an outer and an inner side surface, an outer and an inner medial surface. Preferably, the outer side surface is curvilinear in shape connecting the outer rear surface and the inner front surface defining a continuous, curved surface. The outer medial surface, in turn, defines a continuous, curved surface connecting the outer rear surface and the outer front surface. The ring-shaped tibial filler, having to necessarily fit to the anatomy of the patient who will be implanted, can have different sizes depending on the specific sizes of the bone structure of the patient. It should be noted that the distal part of the tibial filler can have notches, depressions, steps, according to the need. At its central position, the tibial filler has a hollow end-opened channel within which part of the joint element is accommodated, in this example the stem of a tibial component.

The structure of the tibial filler disclosed by the above U.S. Pat. No. 8,506,645 is made of trabecular metal. This type of material has a predetermined porosity that features the entire volume of the tibial filler and which makes it particularly suitable to accommodate the osteoblasts therein in such a way that it is possible to promote bone growth around and inside the tibial filler. In this way, the tibial filler is incorporated into the bone of the patient, forming a single body therewith, with great benefits for the rigidity of the tibia bone and improved characteristics in terms of mechanical response to the stresses. The formation of a single body between the tibial filler and the bone of the patient is crucial for the success of this type of procedures.

To give more stability to the tibial filler and stem assembly, it is possible to inject, between the inner walls of the hollow central channel and the stem, a bone cement. However, the presence of the porosity passing throughout the volume of the tibial filler makes it possible that, during the injection of the cement, significant quantities of the latter infiltrate through the porosity of the trabecular metal up to permeate the volume of the tibial filler and to reach the contact with the bone. This phenomenon causes osteoblasts no longer find free cavities within the tibial filler in which adhere and promote bone growth, and even in the event of finding some of such cavities, they are not sufficient in number for the bone growth to be such that the tibial filler will be integral with the bone. The above therefore makes the implantation of the prosthesis not stable and gives rise to the risk of possible, even serious and painful, drawbacks for the patient, up to the possibility of having to repeat the surgery.

One attempt to address this drawback includes U.S. Patent Application Publication No. 2013/0178947 to Monaghan et al., also assigned to Zimmer Inc. This document discloses an implant realized in porous metal capable of being put in place by the use of bone cement. A first embodiment includes the use of two porous layers having different pore sizes; a first layer has a porosity of greater diameter and a second layer has a porosity of smaller diameter. The two layers with different porosity interpenetrate to each other so as to be mutually integrally connected. The difference in diameter between the two porosities limits the leakage of the cement from a layer to the other layer. However, this limitation does not prevent the possible leakage of the cement toward the implant intended to host bone regrowth. In fact, since the bone cement appears as viscous liquid during the laying operation, it will still be able to infiltrate into the area indented to the bone integration. It is clear that, although this difference in size between the porosities can obstruct the moving of the bone cement, it will not be sufficient to prevent the infiltration of bone cements with low viscosity.

A second embodiment disclosed by the document discloses an implant made of a porous material, having two layers with different diameter porosities, joined by an intermediate layer acting solely as a fixing substrate. The intermediate layer has characteristics of flexibility and do not in any way contribute to the rigidity of the structure, but has simply link function between the two porous layers. Both embodiments disclosed by the patent application U.S. Patent Application Publication No. 2013/0178947 are used as bone filler able to replace part of the bone not present in patients affected by specific pathologies, or not present due to needs dictated by the surgical method for the implantation of the prosthesis.

The porous structure of the two layers along with the flexibility of the intermediate connection layer causes the device subject matter of this document not able to withstand the major stresses since it does not have sufficient structural rigidity. Moreover, this lack of structural rigidity makes the device unusable if the bone shows damages not only to the cancellous part but also to the outer cortical part. Indeed, the outer cortical portion has a high structural rigidity to withstand also major stresses, due both to the loads imposed by the body structure and to accidental stresses, such as impacts, falls, etc.

From the above-described drawbacks it is clear the need to provide a multi-layered prosthetic element that is able to remedy the above-described drawbacks. One object of the present invention, in fact, is to provide a multi-layered prosthetic element that is able to withstand major stresses.

Another object of the present invention is to provide a multi-layered prosthetic element that is able to effectively replace the cortical portion of a bone. Further object of the present invention is to provide a multi-layered prosthetic element that is such as to offer the possibility of accommodating the bone cement therein preventing its leakage through the porosities.

Still a possible object of the present invention is to provide an element as described which is capable of being positioned in an eccentric position relative to the bone axis, for example to the tibial canal. It is still an object of the present invention to provide a multi-layered prosthetic element that is able to promote the bone regrowth. Still, an object of this invention to provide a multi-layered prosthetic element that is able to withstand major stresses, to replace the cortical portion of a bone, to obstruct the passage of the bone cement through its porosity, to be preferably eccentric with respect to the axis of the bone, for example the tibial canal, and to promote bone regrowth.

Finally, it is an object of the present invention to provide a multi-layered prosthetic element that is of versatile and convenient use, easy to use, simple and rapid implantation, reliable use, low costs, and simplified construction.

In particular, according to a first aspect, the present invention relates to a multi-layered prosthetic element comprising a central body of substantially truncated conical shape, having a through axial cavity open at both ends which gives the central body a ring-shaped cross-section. The central body comprises an outer portion, made of trabecular metal material, an inner portion, made of trabecular metal material, and an intermediate portion made of metal material without significant porosity. The outer portion and the inner portion are integrally connected to the intermediate portion. The intermediate portion is configured to mechanically resist to stresses transmitted to the inner portion on one side and to the outer portion on the other side.

In accordance with a second aspect, the present invention relates to a tibial prosthesis comprising a multi-layered prosthetic element and a stem suitable for coupling to a tibial part of the prosthesis. The tibial part includes a tibial plateau. The stem is suitable for being received in the through axial cavity in an offset position with respect to the midpoint of the focal axis of the central body.

In accordance with a third aspect, the present invention relates to a method for implanting a tibial prosthesis comprising preparing a tibial prosthesis, inserting the stem within the tibia, preferably in axial position with respect to the axis of the tibia, placing the multi-layered prosthetic element so that the stem is in an offset position with respect to the midpoint of the focal axis of the central body of the multi-layered prosthetic element itself, fixing the tibial part on the stem by means of a possible interposition of elements capable of creating a misalignment between the stem and the tibial plateau. The tibial plateau is offset with respect to the axis of the tibia bone and possibly with respect to the stem.

In one or more of the above aspects, the present invention can have one or more of the following features. Preferably, the intermediate portion is made of the same metal material as the inner portion and the outer portion, for example $Ti_6Al_4V$. In some embodiments, the thickness of the outer portion and the inner portion is comprised between 0.5 and 5.5 millimeters, and the thickness of the intermediate portion is comprised between 0.9 and 4 millimeters.

Preferably, the outer portion, the intermediate portion and the inner portion are integrally connected by means of sintering. In some embodiments, an edge, for example, a proximal edge of the multi-layered prosthetic element, has two notches (13, 14) that are preferably U-shaped and that extend for a substantial part of the axial extension of the central body. The notches are preferably arranged in a symmetric position with respect to the central axis thereof.

Preferably a part of the inner portion not influenced by the presence of the two notches comprises an area having a lower thickness, which extends for a substantial part of the axial extension of the inner portion and configured to facilitate the centering of the multi-layered prosthetic element during the implantation phases. The area having a lower thickness is preferably disposed at a front part or preferably at an anterior part of the multi-layered prosthetic element.

In some embodiments, the central body has a radial elliptic cross-section and defines a through axial cavity having marked eccentricity and symmetry with respect to the focal axis thereof. Preferably, at a first end of the major axis thereof, the central body has a notch and a second end (25), opposite to the first end, exhibits a section of greater thickness and radius of curvature than the first end.

In some embodiments, the chord subtending the section with a greater thickness and radius of curvature is of a length ranging between 45% and 85% of the length of the central body as measured along the major axis of the central body itself. Preferably, the central body is symmetric with respect to its major axis and asymmetric with respect to its minor axis defining, inside the through axial cavity, a portion with a smaller radius of curvature and a portion with a greater radius of curvature. In some embodiments, the chord subtending the section with a greater radius of curvature is of a length ranging between 45% and 85% of the length of the central body as measured along the major axis of the central body itself.

Figure 2:
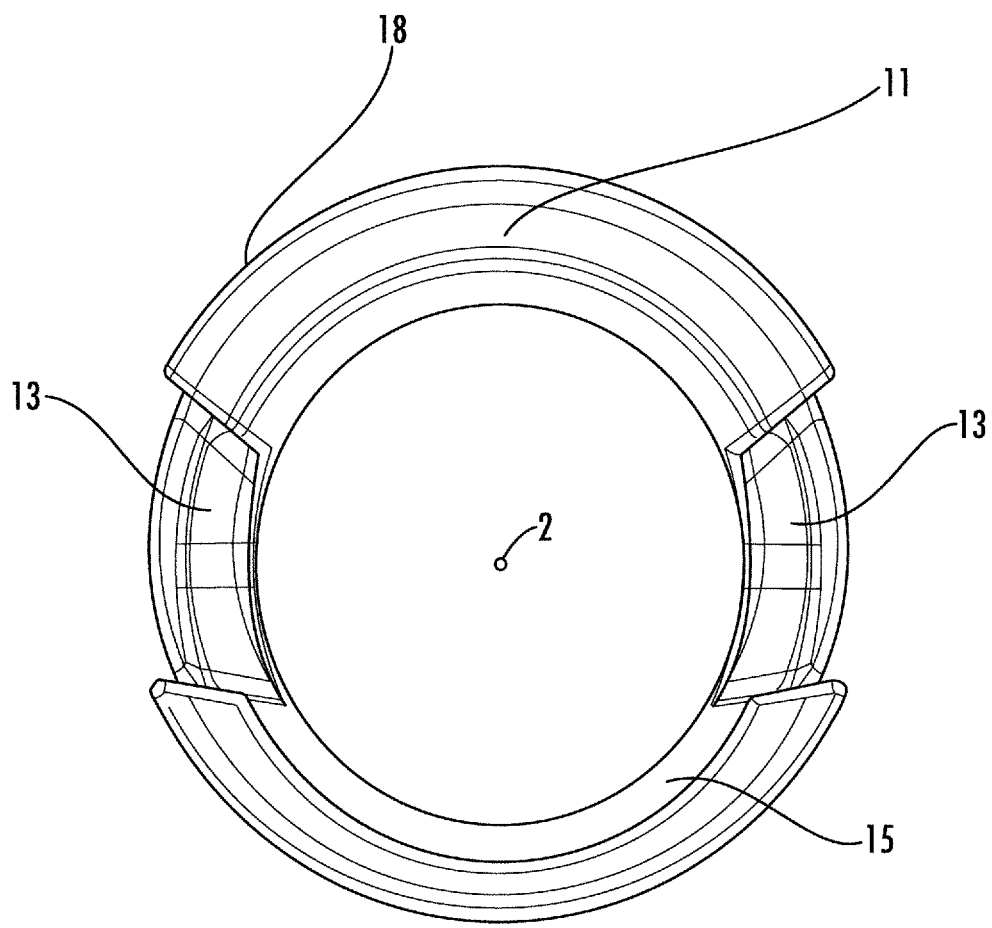
FIG. 2 is a top view of a part of a first embodiment of the present invention.
Figure 4:
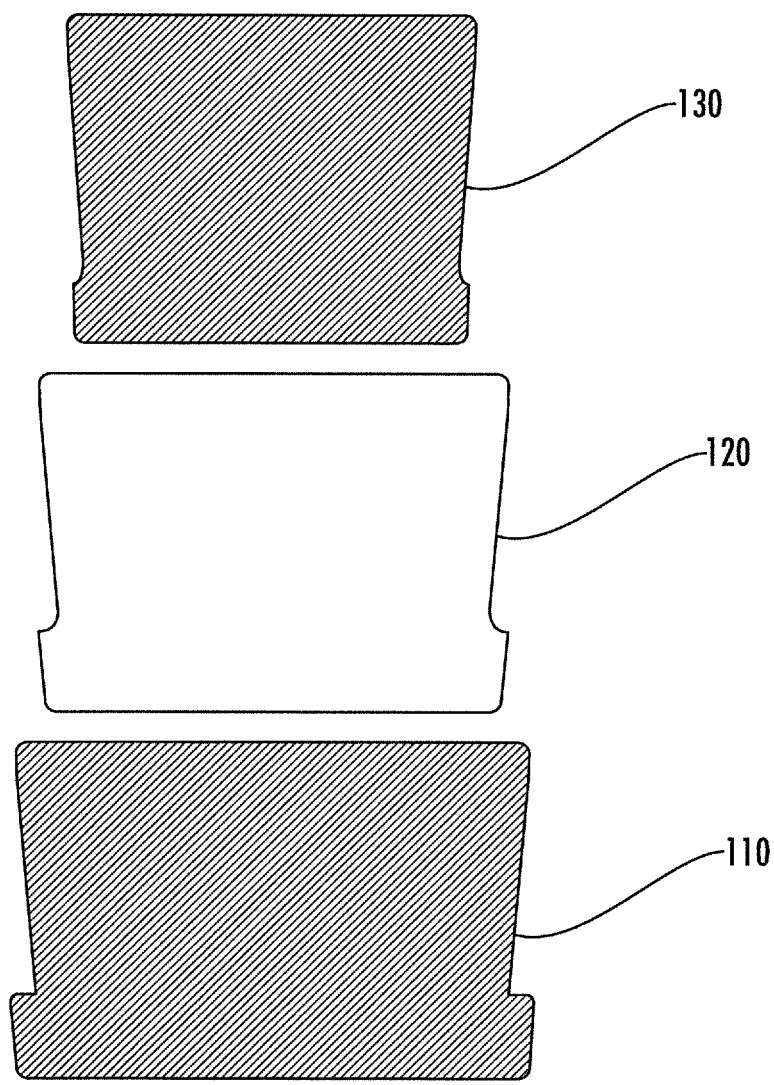
FIG. 4 is an exploded side elevational view of the present invention.

In FIGS. 1 and 2, 100 denotes a multi-layered prosthetic element object of the present invention. It comprises a central body 1 of substantially truncated conical shape, axially hollow, made of metallic material. The central body 1 comprises (FIG. 4) an outer portion 110, made of trabecular metal material, an inner portion 130, made of trabecular metal material, and an intermediate portion 120 made of metal material without significant porosity. The outer 110 and the inner portion 130 are shaped using a known specific processing procedure, for example by EBM (Electron Beam Melting), so that it exhibits a structure with a constant or variable porosity according to the needs. The two outer 110 and inner 130 portions are thus integrally connected to the intermediate portion 120. The connection between the above-mentioned three outer 110, intermediate 120 and inner 130 portions can be done by the use of various known techniques, such as, for example, by sintering. Indeed, the intermediate portion 120 is made of the same metal material as the outer portion 110 and the inner one 130, but has no appreciable porosity. For the above-mentioned portions, 110, 120, 130, the preferred metal material is $Ti_6Al_4V$, that is, a titanium alloy known in the art and here mentioned only by way of non-limiting example. Of course, such preference does not preclude the possibility of using other types of materials for the creation of the outer 110, intermediate 120 and inner 130 portions, or by materials different from each other.

Then, the outer 110, intermediate 120 and inner 130 portions make up the central body 1 of the multi-layered prosthetic element. The central body 1 substantially has: an outer surface 18, made of metallic material and having a porosity, and an inner surface 15, made of metallic material and having a porosity. With reference to the use as an additional element of a tibial prosthesis, the central body has a proximal edge 11 and a distal edge 12.

In some embodiments, the central body 1 has a through axial cavity 2 opened at both ends. The through axial cavity 2 gives the main body 1 of the multi-layered prosthetic element 100 an annular section. In accordance with a possible embodiment, the proximal edge 11 has two U-shaped notches 13 and 14 which extend for a substantial part of the axial multi-layered prosthetic of the central body 1. Preferably the notches 13 and 14 are preferably arranged in a symmetric position with respect to the central axis thereof.

In accordance with a possible embodiment, in a part of the inner portion 130 not affected by the presence of the two notches 13 and 14 there is a zone of reduced thickness 16. The zone of reduced thickness 16, generally located in the front or anterior part of the multi-layered prosthetic element, for example in the case of using as an additional element of a tibial prosthesis, extends for a substantial part of the axial extension of the inner portion 130 and is adapted to ensure the possibility of a perfect centering of the multi-layered prosthetic element during the implantation phases.

Figure 3:
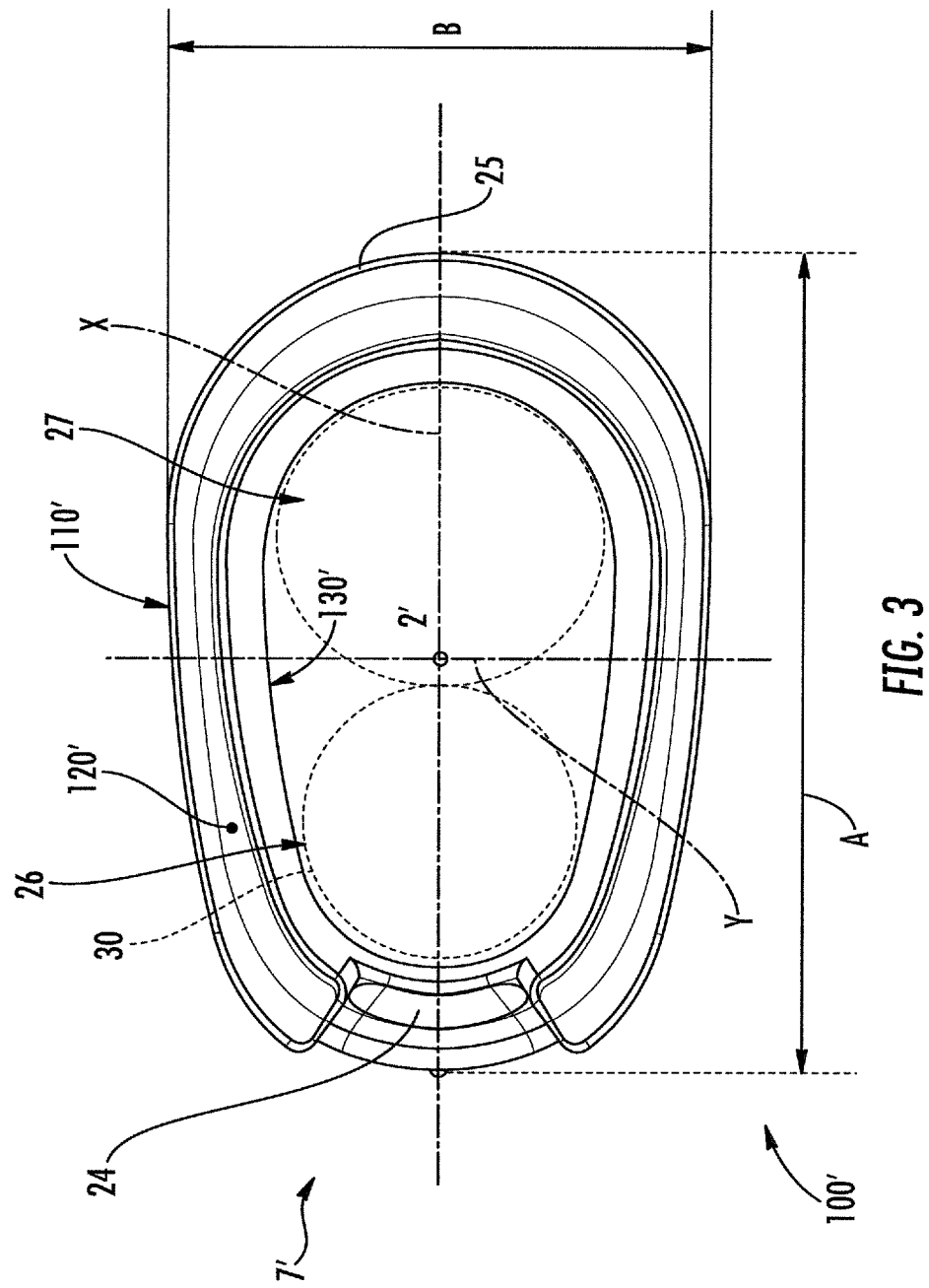
FIG. 3 is a top view of a part of a second embodiment of the present invention.

The multi-layered prosthetic element must adapt to the dimensions of the bone of the patient and will then be available in different sizes. Depending on the size demands, the multi-layered prosthetic element presents variable shape ranging from a truncated conical shape with a circular base (FIGS. 1-2) to a truncated cone with an elliptical base (FIG. 3).

Implantation

Figure 5:
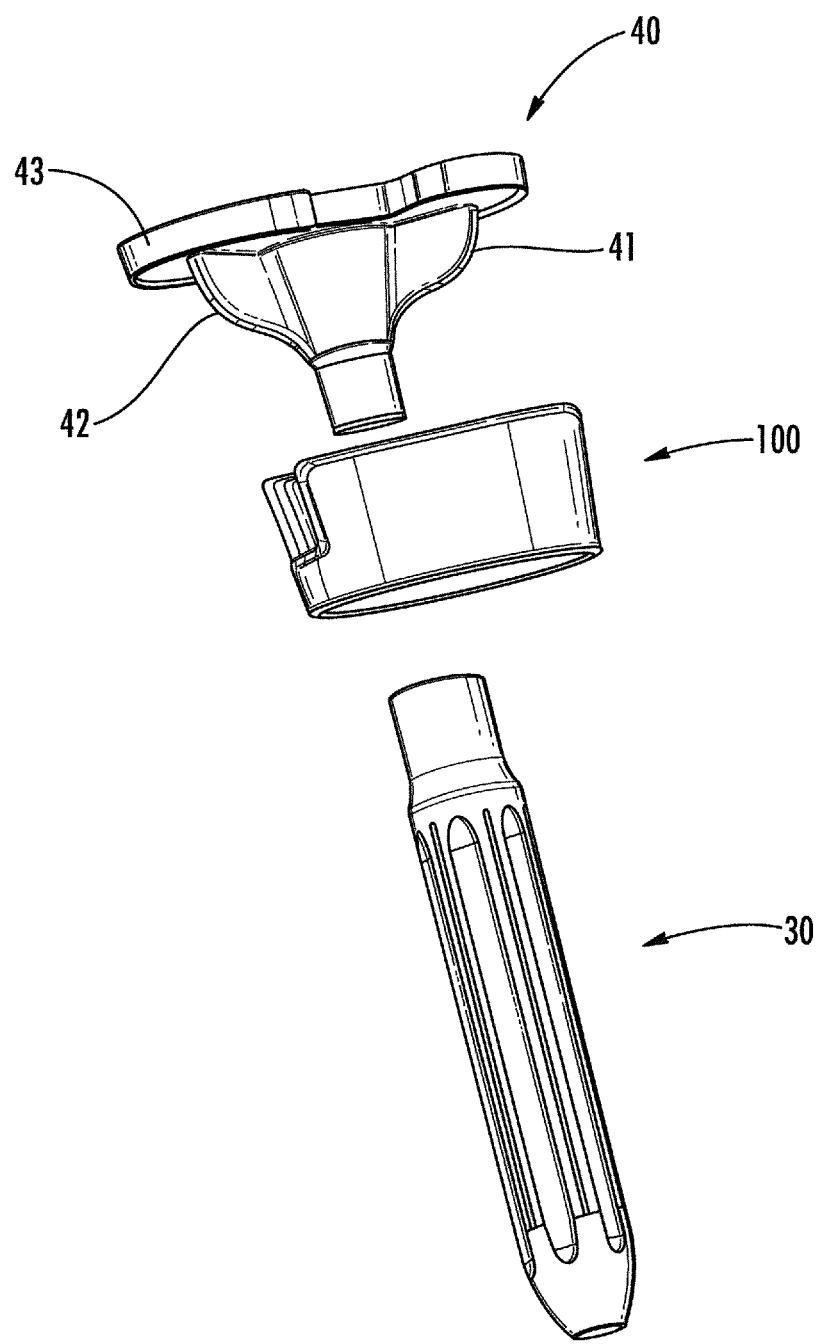
FIG. 5 is an exploded front elevational view of an assembly comprising a variant of the preferred embodiment of the present invention.

The multi-layered prosthetic element is inserted into a bone, for example the tibia, in order to fill and reconstruct large bone deficiencies and bone cavity defects providing a stable base for the positioning of the prosthetic element. Once prepared the site, if necessary, the surgeon provides the arrangement of the multi-layered prosthetic element within the bone. For example, assuming the insertion of the multi-layered prosthetic element of FIG. 1 within a tibia, the outer surface 18 is in contact with the bony part while the inner cavity 2 accommodates a stem 30 adapted to couple to a tibial part 40 of a prosthesis. As can be appreciated from FIG. 5, the tibial part 40 has, in its proximal part to the stem 30, two lugs 41 and 42 to ensure the stability of the tibial plateau 43 with respect to the multi-layered prosthetic element 100 while still maintaining a certain rotational degree of freedom with respect to the axis of the stem 30. Each of the lugs 41 and 42 are received, in fact, within a respective notch 13 and 14 of the central body 1. The lugs 13 and 14 are partially free to move into the notches 13 and 14 while the tibial plateau 43 is juxtaposed to the proximal edge 11. Furthermore, the stem 30 and the tibial part 40 are coupled to each other by shape mating or by fasteners known. After connection, the bone cement injected into the cavity 2 of the main body 1 makes the assembly formed by the stem 30 and the tibial part 40 integral with the multi-layered prosthetic element 100. In fact, the trabecular structure of the inner surface 15 causes the bone cement is received within the porosity of the inner surface 15 to fill it completely and to close, as far as possible, the inner cavity 2. In this way, the bone cement, penetrating inside the porosity of the inner surface 15, and at least partially surrounding the stem 30 and the lugs 41 and 42, once hardened, makes the stem 30 and tibial part 40 assembly integral with the multi-layered prosthetic element 100n ensuring a perfect positioning of the prosthesis.

As above-mentioned, the outer surface 18, as well as the entire outer portion 110, has a trabecular structure. The feature of this structure is the presence of porosity such as to create an appropriate seat so that, once the multi-layered prosthetic element 100 is inserted within the bone, the osteoblasts promotes bone growth within it and in its surroundings in so as to favor, with time, the bone regrowth inside the multi-layered prosthetic element 100.

Likewise, as mentioned, also the inner surface 15, as well as the entire inner portion 130, has a trabecular structure. In this case, the porosity typical of this structure ensures a better adhesion of the bone cement to the multi-layered prosthetic element 100. In fact, the bone cement will be forced to penetrate into the porosity of the inner portion 130, permeating it to fill both the porosity and the axial cavity 2. The presence of the intermediate portion 120 ensures that the bone cement that permeates the porosity of the inner portion 130 cannot reach the porosity of the outer portion 110, therefore acting as a barrier. This barrier function of the intermediate portion 120 is crucial to prevent the cement from occluding the porosity of the outer portion 130, by preventing the proliferation of osteoblasts in its interior, and to promote osseointegration of the multi-layered prosthetic element. The intermediate portion 120 provides mechanical resistance to the forces transmitted from the prosthesis to the inner portion 130 from one side and from the bone to the outer portion 110. Preferably the intermediate portion 120 is made of the same metal material as the inner 130 and outer 110 portions.

In this way it is possible to realize a multi-layered prosthetic element that is able to withstand the relevant stresses to which it is subjected once implanted into the bone. Moreover, the structural rigidity thus conferred to the prosthetic element ensures the distribution uniformity of the loads applied to the tibial plateau.

With reference to the possible embodiments described, both the thickness of the outer portion 110, made of trabecular metallic material, and of the inner portion 130, made of trabecular metallic material, is comprised between 0.5 and 5.5 millimetres. The thickness of the intermediate portion 120 made of metallic material having no significant porosity is comprised between 0.9 and 4 millimetres.

A variant of the present invention is illustrated in FIG. 3 in which a multi-layered prosthetic element 100' is shown. In this FIG. 3, the multi-layered prosthetic element 100' has an elliptical radial section and includes: a central body 1' in turn comprising an outer portion 110', an intermediate portion 120' and an inner portion 130'. As regards the structural characteristics, the materials and the methods of construction, all of these are the same as previously described for the first embodiment.

Figure 6:
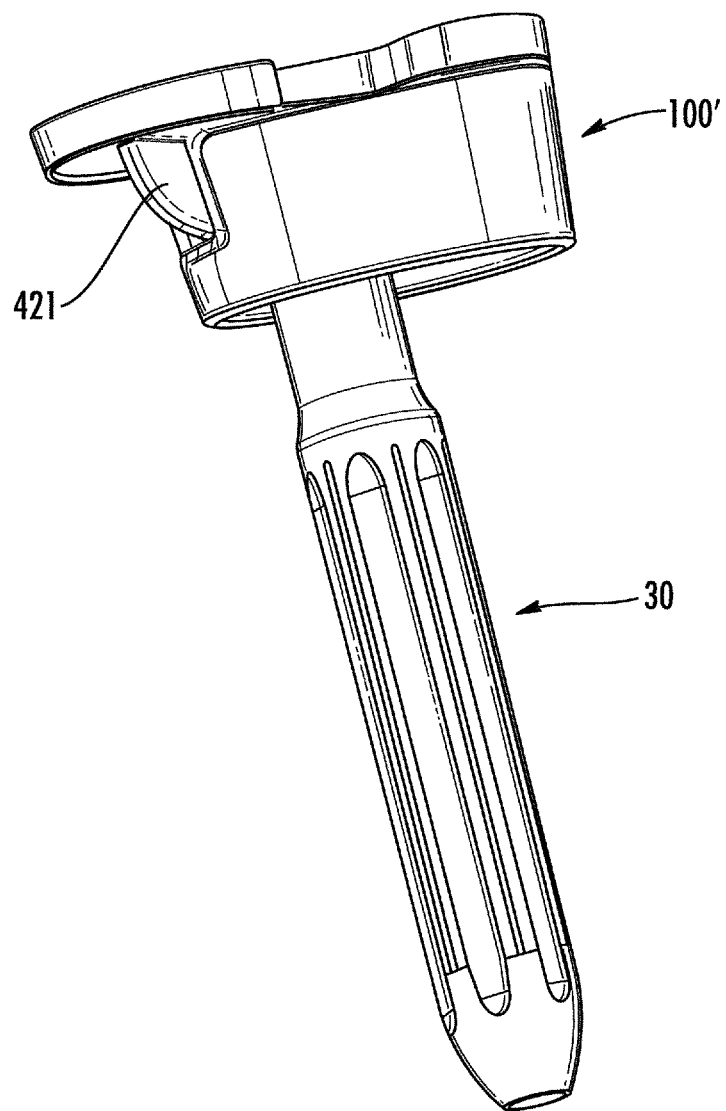
FIG. 6 is a side elevational view of an assembly comprising a variant of the preferred embodiment of the present invention.

The central body 1', comprising a through axial cavity 2', has a marked eccentricity and symmetry with respect to the focal axis thereof. At a first end of its major axis, the central body has a notch 24 suitable to receive a positioning lug 42' (FIG. 6), analogously to what previously described for the two notches 13 and 14. A second end 25, opposite to the notch 24, has a section of greater thickness and radius of curvature than the rest of the central body 1'. Then, with X indicating the major axis of the central body 1', defined by the focal axis of the central body itself, the central body 1' is symmetrical about its major axis X. Y denotes the minor axis, defined by the axis orthogonal to the focal axis of the central body itself, the central body 1' is asymmetrical with respect to its minor axis. This configuration defines, inside the through axial cavity 2', a portion 26 of a lower radius of curvature and a portion 27 of a greater radius of curvature.

The conformation of this variant ensures, during the implantation, by means of the end 25, to replace a portion of damaged cortical bone. In fact, the particular geometric shape of the central body 1 makes possible the perfect centering of the tibial tray 43 mentioned above with respect to the axis of the tibia bone, although the stem 30, integral with the tibial part 40, is received within the cavity 2' in offset position with respect to the midpoint of the focal axis of the central body 1'. In particular, the stem 30 is received within the portion of lower radius of curvature 26 of the through axial cavity 2'. The offset between the stem 30 and the midpoint of the focal axis brings the end 25 to replace the missing part of the cortical area of the bone.

The specific structural strength of the multi-layered prosthetic element 100' makes it possible to the end 25 to withstand the loads on the bone cortex and to possible outer stresses due, for example, trauma and/or contusions.

As regards the embodiment of FIG. 3, indicatively it is possible to use the thickness values indicated for the previous embodiments. Furthermore, with B indicating the chord subtending the end 25, i.e. the area of the central body 1' arranged at the section of a greater radius of curvature 27, B has a value comprised between 45% and 85% of the length A of the central body 1' as measured along the major axis of the central body itself.

Of course, numerous variations can be made in practice with respect to those described and illustrated by way of non-limiting example, without thereby departing from the scope of the present invention and, therefore, from the domain of the present industrial property right.

The invention claimed is:

1. A multi-layered prosthetic element comprising:
a central body having a truncated cone shape, and a through-axial cavity open at both ends;
said central body having a ring-shaped cross-section and a curvilinear vertical outer edge extending longitudinally between the ends;
said central body comprising
an outer portion comprising trabecular metal material,
an inner portion comprising trabecular metal material, and
an intermediate portion comprising trabecular metal material and having a porosity level without significant porosity causing said intermediate portion to form a barrier for bone cement;
the outer portion and the inner portion being coupled to the intermediate portion;
said intermediate portion to mechanically resist stresses transmitted to the inner portion and the outer portion;
said inner portion being radially within said intermediate portion, and said intermediate portion being radially within said outer portion;
said outer portion, said intermediate portion, and said inner portion each comprising a same trabecular metal material; said central body defining opposing longitudinal sides, each opposing longitudinal side defining a U-shaped recess, the U-shaped recesses being arranged symmetrically.

2. The multi-layered prosthetic element according to claim 1, wherein said same trabecular metal material comprises $Ti_6Al_4V$.

3. The multi-layered prosthetic element according to claim 1, wherein a thickness of the outer portion and the inner portion is between 0.5 and 5.5 millimeters, and a thickness of the intermediate portion is between 0.9 and 3 millimeters.

4. The multi-layered prosthetic element according to claim 1, wherein the inner portion has an edge adjacent the U-shaped recesses, the edge having a thickness greater than that of other portions of the inner portion.

5. The multi-layered prosthetic element according to claim 1, wherein the outer portion, the intermediate portion, and the inner portion each comprises a separate layer of the multi-layered prosthetic element.

6. A tibial prosthesis comprising:
a multi-layered prosthetic element comprising
a central body having a truncated cone shape, a proximal end, a distal end opposite said proximal end, and a through-axial cavity open at both of said proximal and distal ends;
said central body having a ring-shaped cross-section and a curvilinear vertical outer edge extending longitudinally between said proximal and distal ends;
said central body comprising
an outer portion comprising trabecular metal material,
an inner portion comprising trabecular metal material, and
an intermediate portion comprising trabecular metal material and having a porosity level without significant porosity causing said intermediate portion to form a barrier for bone cement,
the outer portion and the inner portion being coupled to the intermediate portion,
said intermediate portion to mechanically resist stresses transmitted to the inner portion and the outer portion;
said inner portion being radially within said intermediate portion, and said intermediate portion being radially within said outer portion,
said outer portion, said intermediate portion, and said inner portion each comprising a same trabecular metal material, said central body defining opposing longitudinal sides, each opposing longitudinal side defining a U-shaped recess, the U-shaped recesses being arranged symmetrically; and
a stem configured to be received in the through-axial cavity.

* * * * *